United States Patent
Greenwood-Van Meerveld

(10) Patent No.: US 7,251,529 B2
(45) Date of Patent: Jul. 31, 2007

(54) SPINAL CORD STIMULATION AS TREATMENT FOR FUNCTIONAL BOWEL DISORDERS

(75) Inventor: Beverley Greenwood-Van Meerveld, Oklahoma City, OK (US)

(73) Assignee: Oklahoma Foundation for Digestive Research, Oklahoma City, OK (US)

( * ) Notice: Subject to any disclaimer, the term of this patent is extended or adjusted under 35 U.S.C. 154(b) by 477 days.

(21) Appl. No.: 10/448,448

(22) Filed: May 29, 2003

(65) Prior Publication Data

US 2004/0039425 A1 Feb. 26, 2004

Related U.S. Application Data

(60) Provisional application No. 60/383,813, filed on May 29, 2002.

(51) Int. Cl.
*A61N 1/00* (2006.01)

(52) U.S. Cl. .......................... 607/46; 607/40

(58) Field of Classification Search ............ 607/40–41, 607/46, 117, 133
See application file for complete search history.

(56) References Cited

U.S. PATENT DOCUMENTS

| | | | |
|---|---|---|---|
| 3,654,933 A | 4/1972 | Hagfors | |
| 3,822,708 A | 7/1974 | Zilber | |
| 4,044,774 A | 8/1977 | Corbin et al. | |
| 4,379,462 A | 4/1983 | Borkan et al. | |
| 4,739,764 A * | 4/1988 | Lue et al. | 607/40 |
| 5,031,618 A | 7/1991 | Mullett | |
| 5,058,584 A | 10/1991 | Bourgeois | |
| 5,342,409 A | 8/1994 | Mullett | |
| 5,417,719 A | 5/1995 | Hull et al. | |
| 5,501,703 A | 3/1996 | Holsheimer et al. | |
| 6,002,964 A * | 12/1999 | Feler et al. | 607/46 |
| 6,194,382 B1 * | 2/2001 | Crain et al. | 514/2 |
| 6,233,488 B1 * | 5/2001 | Hess | 607/58 |
| 6,353,762 B1 | 3/2002 | Baudino et al. | |
| 6,558,390 B2 | 5/2003 | Cragg | |
| 6,735,474 B1 * | 5/2004 | Loeb et al. | 607/41 |
| 2002/0116030 A1 * | 8/2002 | Rezai | 607/9 |

OTHER PUBLICATIONS

Meyerson, B. A. et al. "Electric Stimulation of the Central Nervous System," (Undated but believed to be prior art) Karolinska Institute Center for Pain Research Dept. of Clinical Neurol., Karolinska Institute/Hospital (Stockholm, Sweden) pp. 269-280.

Al-Chaer, E. D. et al., "Sensitization of postsynaptic dorsal column neuronal responses by colon inflammation," (1997) Neuroreport 8(15):3267-73.

(Continued)

*Primary Examiner*—Carl Layno
*Assistant Examiner*—Yun Haeng Lee
(74) *Attorney, Agent, or Firm*—McAfee & Taft

(57) ABSTRACT

The present invention relates to treatment of visceral pain of gastrointestinal origin, functional bowel disorders and irritable bowel syndrome comprising electrical stimulation of the spinal cord using one or more commercially available and implantable spinal cord stimulation leads for a time period sufficient to suppress or extinguish the pain or symptoms associated with visceral pain of gastrointestinal origin, functional bowel disorders or irritable bowel syndrome.

29 Claims, 5 Drawing Sheets

OTHER PUBLICATIONS

Armour, J.A. et al., "Long-term modulation of the intrinsic cardiac nervous system by spinal cord neurons in normal and ischaemic hearts," (2002) Auton. Neurosci. 95, 71-79.

Azpiroz, F., "Dimensions of gut dysfunction in irritable bowel syndrome: Altered sensory function," (1999) Can J. Gastroenterol. 13 (Suppl. A), 12A-14A.

Barolat, G., "Experience with 509 Plate Electrodes Implanted Epidurally from $C_1$ to $L_1$," (1993) Stereotact. Funct. Neurosurg. 61: 60-79.

Barolat, G. et al., "Epidural Spinal Cord Stimulation in the Management of Spasms in Spinal Cord Injury: a Prospective Study," (1995) Stereotact. Funct. Neurosurg. 64: 153-164.

Bergin, A. J. et al., "Changes in anorectal function in persistent bowel disturbance following salmonella gastroenteritis," (1993) Eur. J. Gastroenterol. Hepatol. 5: 617-620.

Bueno, L. et al., Effects of inflammatory mediators on gut sensitivity. (1999) Can J. Gastroenterol; 13 (Suppl A) 42A-46A.

Cervero, F., "Visceral Pain: Mechanisms of Peripheral and Central Sensitization," (1995) Ann. Med. 27: 235-239.

Croom, J. E. et al., "Cutaneous blood flow increases in the rat hindpaw during dorsal column stimulation," (1996) Brain Res. 728: 281-286.

Cui, J.G., et al., "Effects of spinal cord stimulation on touch-evoked allodynia involve GABAergic mechanisms," An experimental study in the mononeuropathic rat. (1996) Pain 66, 287-295.

Dubussion, D., "Effect of dorsal-column stimulation on gelatinosa and marginal neurons of cat spinal cord," (1989) J. Neurosurg. 70: 257-265.

Foreman, R. D. et al., "Modulation of intrinsic cardiac neurons by spinal cord stimulation: implications for its therapeutic use in angina pectoris," (2000) Cardiovasc. Res. 47: 367-375.

Gebhart, G. F., "Physiology, Pathophysiology, and Pharmacology Visceral Pain," (2000) Reg. Anesth Pain Med. 25: 632-638.

Gibson, M.S. et al., "An acute inflammatory insult induces long term colonic hypersensitivity," (2000) Oklahoma Foundation for Digestive Research Basic Science Labs, VA Medical Center, Oklahoma City, OK.

Greenwood-Van Meerveld, B. et al, "Stereotaxic delivery of corticosterone to the amygdala modulates colonic sensitivity in rat," (2001) Brain Res. 893: 135-142.

Greenwood-Van Meerveld, B. et al., "CRF-1 Receptor-Mediated Mechanisms Regulate Post-Inflammatory Visceral Hypersensitivity in Rats," (2002) American Gastroenterological Association Plenary Session. San Francisco, vol. 122(4).

Greenwood-Van Meerveld, B. et al., "Attenuation by spinal cord stimulation of a nociceptive reflex generated by colorectal distention in a rat model," (2003) Auton. Neurosci. 104: 17-24.

Gue, M. et al., "Stress-induced visceral hypersensitivity to rectal distension in rats: role of CRF and mast cells," (1997) Neurogastroenterol Motil. 9, 271-279.

Gunter, W. D. et al., "Evidence for visceral hypersensitivity in hip-anxiety rats," (2000) Physiol. Behav. 69, 379-382.

Gweek, K. A., et al., "Psychometric scores and persistence of irritable bowel after infectious diarrhoea," (1996) Lancet 347, 150-153.

Illis, L. S., "Rehabilitation Following Brain Damage: Some Neurophysiological Mechanisms. The Effects of Repetitive Stimulation in Recovery from Damage to the Central Nervous System," (1982) Int. Rehabil. Med. 4, 178-184.

Katz, P. G. et al., "Effect of Implanted Epidural Stimulator on Lower Urinary Tract Function in a Spinal-Cord-Injured Patients," (1991) Eur. Urol. 20: 103-106.

Kellow, J. E. et al., "Altered Small Bowel Motility in Irritable Bowel Syndrome is Correlated with Symptoms," (1987) Gastroenterology 92: 1885-1893.

Kellow, J. E. et al., "Dysmotility of the small intestine in irritable bowel syndrome," (1988) Gut 29: 1236-1243.

Langlois, A. et al., "Response heterogeneity of $5\text{-}HT_3$ receptor antagonists in a rat visceral hypersensitivity mode," (1996) Eur. J. Pharmacol. 318, 141-144.

Lembo, T. et al., "Symptom Duration in Patients with Irritable Bowel Syndrome," (1996) Am. J. Gastroenterol. 91, 898-905.

Lindblom, U. et al., "The effect of dorsal column stimulation on the nociceptive response of dorsal horn cells and its relevance of pain suppression.," (1977) Pain 4: 133-144.

Linderoth, B. et al., "Tachykinin release from rat spinal cord in vitro and in vivo in response to various stimuli," (1988) Regul. Pept. 21, 129-140.

Linderoth, B. et al., "Peripheral Vasodilatation after Spinal Cord Stimulation: Animal Studies of Putative Effector Mechanisms," (1991) Neurosurgery 28(2), 187-195.

Linderoth, B. et al., "Effects of Sympathectomy on Skin and Muscle Microcirculation during Dorsal Column Stimulation: Animal Studies," (1991) Neurosurgery 29(16), 874-879.

Linderoth, B. et al., "An animal Model for the Study of Brain Transmittor Release in Response to Spinal Cord Stimulation in the Awake, Freely Moving Rat: Preliminary Results from the Periaqueductal Grey Matter," (1993) Acta. Neurochir. Suppl. (Wien.) 58: 156-160.

Linderoth, B. et al., "Sympathetic Mediation of Peripheral Vasodilation Induced by Spinal Cord Stimulation: Animal Studies of the Role of Cholinergic and Adrenergic Receptor Subtypes," (1994) Neurosurgery 35(14), 711-719.

Linderoth, B. et al., "Physiology of Spinal Cord Stimulation," (1999) Review and update. Neuromodulation 2(3), 150-164.

Linderoth, B. et al., "Spinal Cord Stimulation: Mechanisms of Action," (2002) In: Burchiel, K. (Ed.), Surgical Management of Pain. Thieme Medical Publishers, Inc., New York, pp. 505-526. Chapter 39.

Mayer, E. A. et al., "Basic and Clinical Aspects of Visceral Hyperalgesia," (1994) Gastro. 107: 271-293.

Meglio, M. et al., "Epidural Spinal Cord Stimulation for the Treatment of Neurogenic Bladder," (1980) Acta Neurochir. (Wien) 54, 191-199.

Melzack, R. et al., "Pain Mechanisms: A New Theory," (1965) Science 150, 971-979.

Mendeloff, A. L. et al., "Epidermiology of Functional Gastrointestinal Disorders. In: Chey W.Y. ed. Functional Disorders of the Digestive Tract," (1983) New York: Raven Press pp. 13-19.

Mertz, H. et al., "Altered Rectal Perception is a Biological Marker of Patients with IBS," (1995) Gastro. 109: 40-52.

Meyerson, B. A. et al., "Electric stimulation of the central nervous system," (1999) In: Max, M. (Ed.), PAIN 1999-an Updated Review Textbook for IASP refresher Course. $9^{th}$ World Congress on Pain, Vienna, Austria. IASP Press, Seattle, pp. 269-280.

Meyerson, B.A. et al., "Mechanisms of spinal cord stimulation in neuropathic pain," (2000) Neurol. Res. 22, 285-292.

Ness, T. J. et al, "Colorectal distention as a noxious visceral stimulus: physiologic and pharmacologic characterization of the pseudoaffective reflexes in the rat," (1988) Brain Research 450: 153-169.

Ness, T. J. et al., "Acute inflammation differentially alters the activity of two classes of rat spinal visceral nociceptive neurons," (2000) Neurosci. Lett, 281, 131-134.

Ness, T. J. et al., "Inflammation enhances reflex and spinal neuron responses to noxious visceral stimulation in rats," (2001) Am. J. Physiol 280(4):G649-57.

North, R. D. et al., "Spinal cord stimulation for chronic pain," (2000) In: Schmidek, H.H. (Ed.), Schmidek and Sweet's Operative Neurosurgical Techniques, $4^{th}$ ed. Saunders, Philadelphia, pp. 2407-2422.

Plourde, V. et al., "Calcitonin gene-related peptide in viscerosensitive response to colored distension in rats," (1997) Am. J. Physiol. 273, G191-G196.

Prior, A. et al., "Anorectal manometry in irritable bowel syndrome: differences between diarrhoea and constipation predominant subjects," (1990) Gut 31, 458-462.

Read, D. J. et al., "The Effect of Spinal Cord Stimulation on Function in Patients with Multiple Sclerosis," (1980) Brain 103, 803-833.

Ritchie, J., "Pain from distension of the pelvic colon by inflating a balloon in the irritable colon syndrome," (1973) Gut 14, 125-132.

Roza et al., "Substance P. calcitonin gene related peptide and PGE$_2$ co-released from the mouse colon: a new model to study nociceptive and inflammatory response in viscera, in vrito," (2001) Pain; 93(3):213-219.

Saade, N. et al., "Inhibition of nociceptive withdrawal flexion reflexes through a dorsal column-brainstem-spinal loop," (1985) Brain Res. 335, 306-308.

Sandler, R. S., "Epidemiology of Irritable Bowel Syndrome in the U.S.," (1990) Gastroenterology 99(2): 409-415.

Siegfried, J., "Treatment of spasticity by dorsal cord stimulation," (1980) Int. Rehabil. Med. 2, 31-34.

Siegfried, J. et al., "Electrical Spinal Cord Stimuilation for Spastic Movement Disorders," (1978) Appl. Neurophysiol. 41, 134-41.

Siegfried, J. et al., "Electrical Spinal Cord Stimulation for Spastic Movement Disorders," (1980) Appl. Neurophysiol. 44, 77-92.

Stiller, C. O. et al., "Release of Gamma-Aminobutyric Acid in the Dorsal Horn and Suppression of Tactile Allodynia by Spinal Cord Stimulation in Mononeuropathic Rats," (1996) Neuropsurgery 39(12), 367-374.

Talley, N. J. et al., "Epidemiology of Colonic Symptoms and the Irritable Bowel Syndrome," (1991) Gastro. 101:927-934.

Tanaka, S. et al., "Low intensity spinal cord stimulation may induce cutaneous vasodilation via CGRP release," (2001) Brain Res. 896, 183-187.

Traub, R. J. et al., "Fos-like proteins in the lumbosacral spinal cord following noxious and non-noxious colorectal distention in the rat," (1992) Pain 49, 393-403.

Traub, R. J. et al., "Differential expression of c-Fos and c-jun in two regions of the rat spinal cord following noxious colorectal distension," (1993) Neurosci. Lett. 160, 121-125.

Traub, R. J. et al., "Noxious colorectal distention induced c-fos protein in limbic brain structures in the rat," (1996) Neurosci. Letters 215:165-168.

Whitehead, W.E., et al., "Irritable bowel syndrome: Definition of the syndrome and relations to other disorders," (1985) In: GI Disorders: Behavioral and Physiological Basis for Treatment. New York: Academic Press, 155-177.

Whitehead, W.E. et al., "Tolerance for rectosigmoid distention in irritable bowel syndrome," (1990) Gastroenterology 98, 1187-1192.

Yashnitsa, V. et al., "Spinal cord stimuation attenuates dorsal horn neuronal hyperexcitability in a rat model of mononeuropathy," (1999) Pain 79, 223-233.

Spinal Cord Stimulation for Pain Management, http://www.ncbi.nlm.nih.gov/books/bv.fcgi?rid=hstat6.section.1307 (last visited Sep. 19, 2006). Source: The National Library of Medicine Website.

U.S. Patent No. 5,417,719, col. 7, lines 19-35.

U.S. Patent No. 5,501,703, claims 13-15, 22-24, 27-29, 33-35, 41-42 and 54-56; col. 3, line 65—col. 4, line 2.

U.S. Patent No. 5,643,330, claims 13-15, 21-23, 25-27, 29-31, 35-36 and 45; col. 3, line 66—col. 4, line 8.

*Atlas Powder Co. v. Ireco, Inc.*, 190 F.3d 1342, 1347, 51 U.S.P.Q.2d 1943, 1947 (Fed. Cir. 1999).

*In re Best*, 562 F.2d 1252, 1254,195 U.S.P.Q. 430, 433 (C.C.P.A. 1977).

MPEP § 2112.

MPEP § 2112.IV citing *Ex parte Levy*, 17 U.S.P.Q.2d 1461, 1464 (Fed. Cir. 1990).

*Toro Co. v. Deere*, 69 U.S.P.Q.2d 1584, 1590-1591 (Fed. Cir. 2004).

MPEP § 2112.IV.

*Elan Pharmaceuticals, Inc. v. Mayo Foundation for Medical Education and Research*, 304 F.3d 1221, 1229, 64 U.S.P.Q.2d 1292, 1297 (Fed. Cir. 2002) (further citations omitted).

*Dewey & Almay Chemical Co. v. Mimex Co.*, 124 F.2d 986, 989 (2d. Cir. 1942).

*In re Rijckaert*, 9 F.3d 1531, 1534, 28 USPQ2d 1955, 1957 (Fed. Cir. 1993).

*In re Robertson*, 169 F.3d 743, 745, 49 USPQ2d 1949, 1950-51 (Fed. Cir. 1999) (citations omitted).

Sylvie Bradesi, PhD et al., *Inflammatory Bowel Disease and Irritable Bowel Syndrome: Separate or Unified?*, Jul. 15, 2003, http://www.medscape.com/viewarticle/457728.

*Irritable Bowel Syndrome Defined* at http://www.nlm.nih.gov/medlineplus/ency/article/000246.htm (last visited Sep. 19, 2006).

Dr. Jenifer K. Lehrer and Dr. Gary R. Lichtenstein, *Irritable Bowel Syndrome*, updated Jun. 29, 2005, http://www.emedicine.com/MED/topic1190.htm.

Norma Gaetani, *IBS and IBD: Two Very Different Disorders*, Oct. 6, 2005, available at http://www.ccfa.org/about/news/ibsoribd.

*Inflammatory Bowel Disease Defined* at http://www.nlm.nih.gov/medlineplus/ency/article/000249. htm·Definition (last visited Sep. 19, 2006).

About Incontinence Organization, *Prevalence of Bowel Incontinence*, Mar. 3, 2003, http://www.aboutincontinence.org/prevalence.html.

American Society of Colon & Rectal Surgery Website, *Bowel Incontinence*, http://ascrs.affiniscape.com/displaycommon.cfm?an=1&subarticlenbr=5 (last visited Sep. 19, 2006).

Dr. Manish K. Singh et al., *Chronic Pelvic Pain*, last updated Mar. 2, 2006 http://www.emedicine.com/MED/topic2939.htm.

Jerome Weiss, MD, UCSF Medical Center and the Pacific Center for Pelvic Pain and Dysfunction, *Questions and Answers on Pelvic Floor Dysfunction*, Aug. 4, 1999, http://www.ic-network.com/guestlectures/weiss.html.

MPEP § 2142.

MPEP § 2143.

*In re Vaeck*, 947 F.2d 488, 20 USPQ2d 1438 (Fed. Cir. 1991).

\* cited by examiner

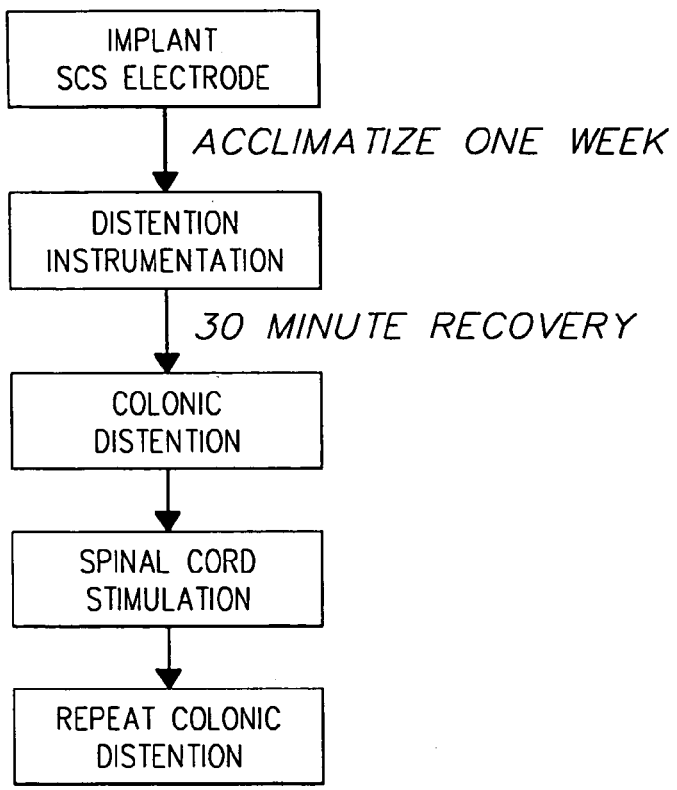
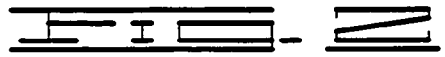
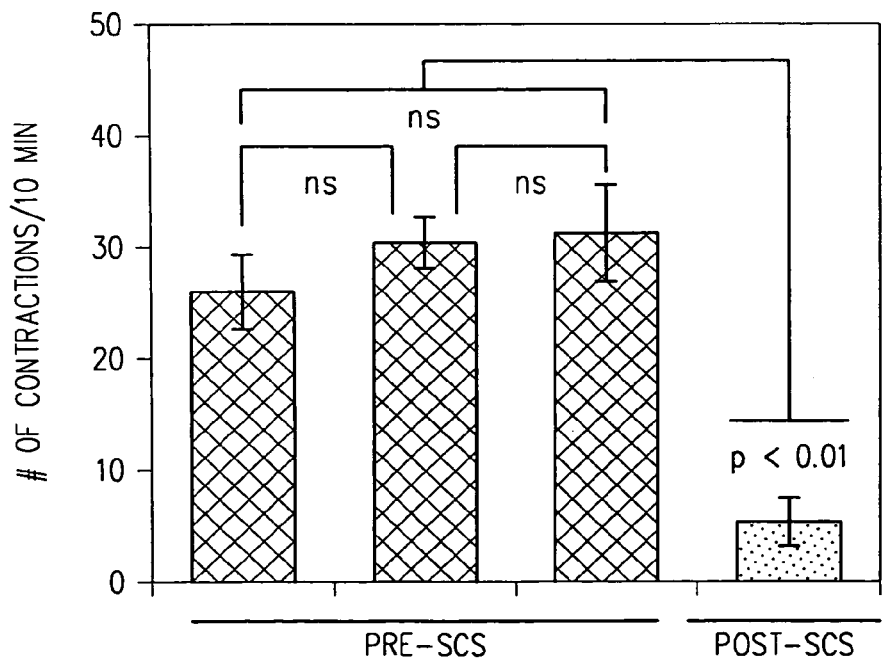
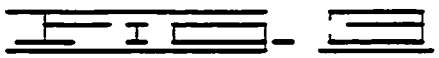

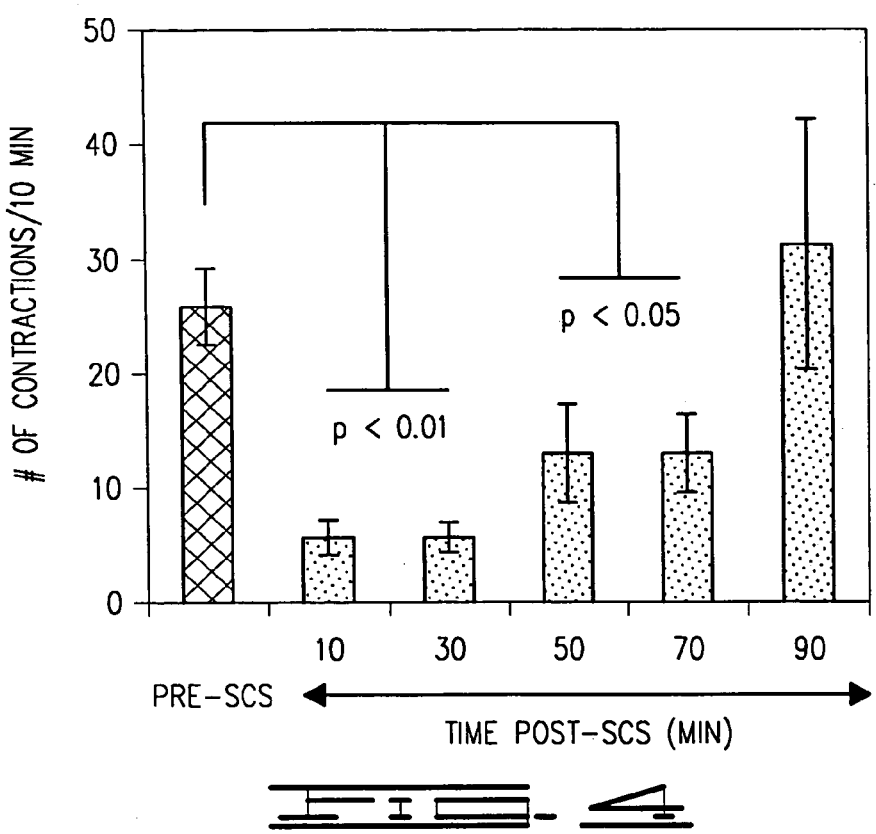
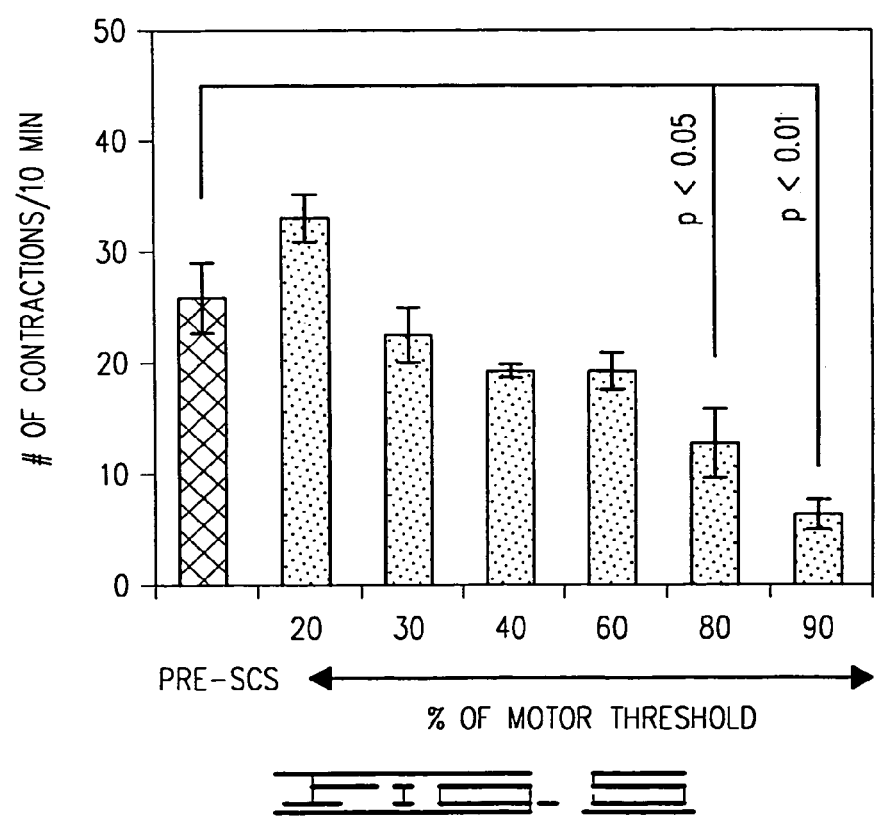

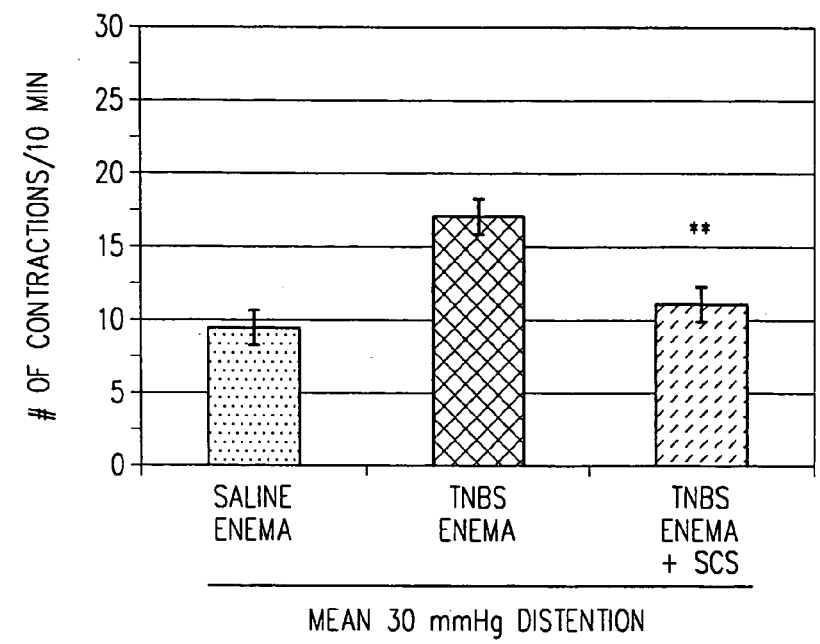
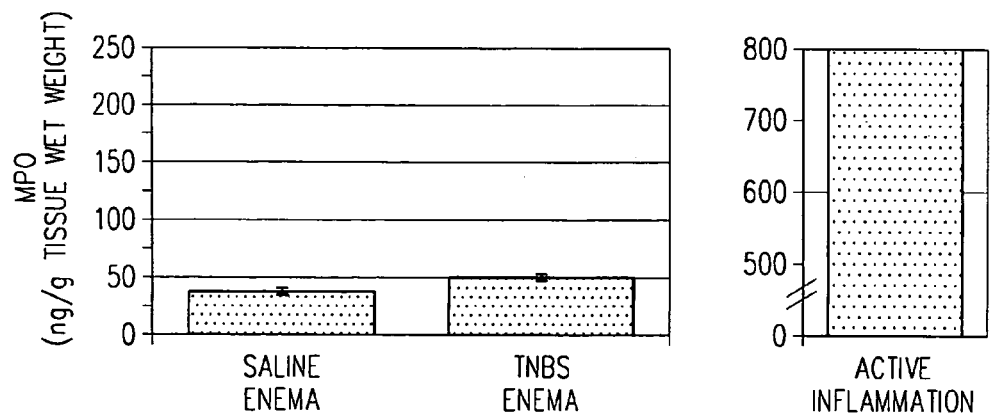
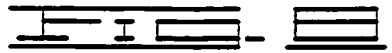

SPINAL CORD STIMULATION AS TREATMENT FOR FUNCTIONAL BOWEL DISORDERS

This application claims the benefit of U.S. Provisional Application No. 60/383,813 entitled METHOD FOR USING SPINAL CORD STIMULATION TO RELIEVE VISCERAL PAIN filed on May 29, 2002.

BACKGROUND OF THE INVENTION

This invention relates generally to techniques for providing treatment therapy to neural tissue to relieve visceral pain, and more particularly, but not by way of limitation, to spinal cord stimulation for the treatment of visceral pain of gastrointestinal origin, functional bowel disorders and irritable bowel syndrome.

Functional bowel disorders, including irritable bowel syndrome, are common abnormalities of the gastrointestinal tract that are associated with severe and chronic abdominal pain. It has been estimated that a minimum of 10-20% of the United States population experience several of the symptoms of functional bowel disorders. Moreover, greater than 30% of patients that recover from an acute infectious gastroenteritis also exhibit irritable bowel syndrome symptomatology. Symptoms of irritable bowel syndrome include abdominal cramping with pain that is concurrent with abnormal bowel habits in terms of frequency and appearance.

Treatments for functional bowel disorders generally, and irritable bowel syndrome specifically, include modification of diet, psychological therapy, stress management, exercise, antidepressant and antianxiety medications, antidiarrheals, bile acid binding agents, anticholinergics, some experimental medications, and other pharmacological and non-pharmocological treatments. These treatments have only limited success and effectiveness and some have undesirable side effects.

Electrical stimulation of the dorsal columns of the spinal cord (spinal cord stimulation; SCS) has been employed for years to treat chronic severe pain. Currently the applications for spinal cord stimulation include both chronic neuropathic and ischemic pain. The mechanism by which electrical stimulation via an electrode placed on the dorsal surface of the spinal cord provides pain relief is poorly understood but may involve both spinal and supraspinal neural circuits.

The symptoms of irritable bowel syndrome may be due, at least in part, to disturbed intestinal motility, primarily characterized by hypercontractility. Nevertheless, symptoms cannot be explained entirely by changes in motility alone and they may also arise from complex feedback and feedforward interactions between supraspinal circuits, the spinal cord and the periphery.

Abnormal (or heightened) visceral sensory perception is a more recent mechanism that has been proposed to account for many of the symptoms of irritable bowel syndrome. The concept of abnormal pain perception in irritable bowel syndrome is supported by the observation that gastrointestinal distention in patients with irritable bowel syndrome evokes pain at lower distention pressures compared to asymptomatic control subjects. It may be that the development of gastrointestinal sensitization initiates the process of abdominal pain and concomitant abnormal gastrointestinal function seen in irritable bowel syndrome patients.

Visceral allodynia (nonpainful response perceived as painful) and hyperalgesia (heightened response to a painful stimulus) in patients with irritable bowel syndrome has been postulated to develop as a result of an acute irritating event followed by development of hypersensitivity of undamaged tissues. The increased sensitivity could occur as the result of central and/or peripheral mechanisms. A manifestation of these changes is that responses to colorectal distention are accentuated in animals with visceral hypersensitivity. For example, colonic inflammation with mustard oil has been found to increase the background activity in lumbosacral postsynaptic dorsal column neurons and potentiated the evoked responses to colorectal distention.

In response to sensitization, innocuous colorectal distentions evoke a visceromotor behavioral response, which resemble those induced by nociceptive stimuli in non-sensitized rats. This suggests that alterations in neuronal activity within the spinal cord may be involved in processing information from the colon, and that induced abnormalities in spinal neuronal processing may lead to the development of visceral hypersensitivity. Furthermore, recent animal studies have shown that nociceptive distention of the colon produces an increase in cFos expression (a gene marker indicating enhanced neuronal excitability) in the lumbosacral spinal cord suggesting enhanced neuronal excitability. Pharmacotherapy of similar symptoms encountered in man often fails, and spinal cord stimulation besides its beneficial effects on various types of pain also has proven effective in suppressing hyperexcitable somatosensory reflexes in spasticity.

Despite studies and postulates, however, chronic visceral pain of gastrointestinal origin is poorly understood and lacks an effective therapy. Thus, there is a need for improved treatment for visceral pain of gastrointestinal origin, functional bowel disorders and irritable bowel syndrome.

SUMMARY OF THE INVENTION

The present invention provides spinal cord stimulation as treatment for visceral pain of gastrointestinal origin, functional bowel disorders and irritable bowel syndrome which meet the needs described above and overcome the shortcomings of the prior art.

The present invention relates to treatment of visceral pain of gastrointestinal origin, functional bowel disorders and irritable bowel syndrome comprising electrical stimulation of the spinal cord or nervous system of the patient using one or more commercially available and implantable spinal cord stimulation leads for a time period sufficient to suppress or extinguish pain or symptoms associated with visceral pain of gastrointestinal origin, functional bowel disorders or irritable bowel syndrome. This inventive treatment may be used either alone or combination with pharmacological and non-pharmocological treatments.

This inventive treatment may use one or more implantable leads comprised of a plurality of conducting electrodes adapted for accurate placement within the human body, in particular the area of the spinal cord or nervous system to be stimulated. Various devices for spinal cord stimulation used in chronic pain management, movement disorders and substance addiction are disclosed in U.S. Pat. Nos. 3,654,933, 4,044,774, 4,379,462, 5,058,584, 5,417,719, 5,501,703, 5,643,330 and 6,233,488 B1, which are all incorporated by referenced herein in their entirety.

It is therefore a general object of the present invention to provided improved spinal cord stimulation as treatment for visceral pain of gastrointestinal origin, functional bowel disorders and irritable bowel syndrome. Other and further objects, features and advantages of the present invention

BRIEF DESCRIPTION OF THE DRAWINGS

FIG. 2 is a schematic illustration of the experimental design used to investigate the effect of spinal cord stimulation (spinal cord stimulation) on colonic sensitivity monitored as a visceromotor behavioral response in rats.

FIG. 3 illustrates the effect of spinal cord stimulation (90% motor threshold, for 30 minutes) on the visceromotor behavioral response produced by distending a balloon in the colon to a nonciceptive level of 60 mm Hg distention pressure for 10 minutes. Following spinal cord stimulation there was a significant (P<0.001) inhibitory effect in the number of abdominal contractions during a 10-minute recording period in response to the colonic stimulus in 5 chronically implanted, fully conscious and freely moving rats.

FIG. 4 illustrates the optimal threshold-response effect of spinal cord stimulation on the visceromotor behavioral response produced by distending a balloon in the colon to a pressure of 60 mm Hg for 10 minutes spinal cord stimulation caused an attenuation of the number of abdominal contractions during a 10-minute recording period that reached statistical significance at 80% motor threshold (P<0.01). The maximal inhibitory effect of spinal cord stimulation occurred at 90% motor threshold. Data were obtained from 5 rats.

FIG. 5 illustrates the duration of the inhibitory effect following spinal cord stimulation (90% motor threshold for 30 minutes) on the visceromotor behavioral response produced by distending a balloon in the colon to a pressure of 60 mm Hg. Seventy minutes following cessation of spinal cord stimulation, there continued to be a significant inhibition in the number of abdominal contractions in response to colonic distention.

FIG. 8 illustrates the effect of spinal cord stimulation (90% motor threshold, 50 Hz, 0.2 ms, for 30 seconds) in rats following recovery from the inflammatory insult spinal cord stimulation caused a significant inhibition of post-inflammatory colonic hypersensitivity as demonstrated by a reduced number of abdominal muscle contractions induced by low levels of colonic distention.

DETAILED DESCRIPTION OF THE PREFERRED EMBODIMENT(S)

Figures 1A, 1B, 1C:
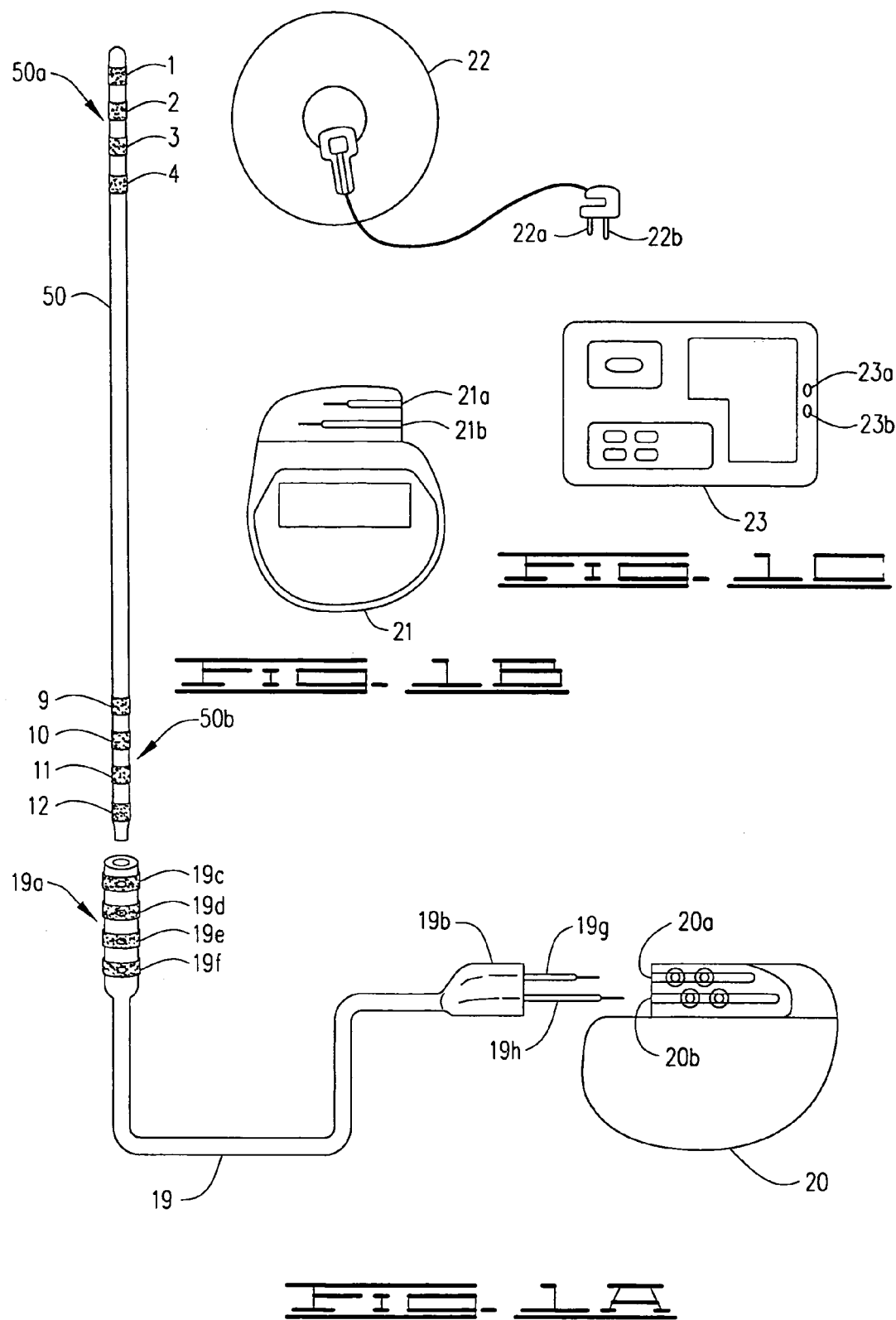
FIG. 1 illustrates schematically a spinal cord stimulation system that may be used in the inventive treatment.

The basic elements needed for the method and application of spinal cord stimulation for treatment of pain and symptoms associated with pain of gastrointestinal origin, functional bowel disorders and irritable bowel syndrome, comprise a spinal cord stimulator lead and a power source connected to the lead to enable conduction of electrical impulses to the spinal cord. The spinal cord stimulator lead contains external contact electrodes at the distal tip which send impulses into the spinal cord. These distal contact electrodes are independently connected to corresponding contact terminals at the proximal end of the lead by separate stranded wires which run substantially parallel to each other. The proximal conductive terminals are in turn connected to an electrical power source through a lead extension connector which makes individual contact with the proximal lead terminals and allows transmission of electrical signals from the power source to the distal lead electrodes.

The generator or electrical source provides electrical stimulation and allows for the selective and independent variation of characteristics of the electrical power including amplitude, frequency rate and pulse width, as well as variation in the polarity of the conducting electrode contacts within the lead (any number of lead contacts from four to eight to sixteen in current technology). Alternatively, it is envisioned that the lead extension connector may be omitted and the electrical power source connected directly to the proximal conductive terminals.

The amplitude of the electrical power (voltage; volts) may be varied. The pulse width of the electrical power (microseconds; ms) may also be varied. The rate of the electrical power (Hertz; Hz) may also be varied. Finally, the duration of the treatment can be varied. All of these factors must be determined for a particular treatment, which is within the knowledge of those skilled in the art without undue experimentation.

The number of leads implanted ranges from one lead to several. Preferably, the number of leads implanted is two.

Preferably, the lead or leads are inserted into the epidural space of the spinal cord and contact the external portion of the dura to stimulate the neural structures underneath. The lead or leads may be inserted into the sacral, caudal, lumbar, thoracic or cervical spines. The position of the implanted lead or leads ranges from the sacral position to the high cervical position of the spinal cord. Preferably, the lead or leads are implanted from the upper lumbar to the lower cervical position in the spinal cord. More preferably, the lead or leads are implanted from the lower thoracic to the higher thoracic position of the spinal cord. Most preferably, the lead or leads are implanted from the lower thoracic to the middle thoracic position in the spinal cord. The lead or leads are positioned so that the lead or leads are parallel to the midline of the spinal cord and may be positioned to the right of the midline, directly on the midline or to the left of the midline. The lead or leads may also be placed oblique or transverse to the midline. If more than one lead is implanted, the leads may be positioned both to the right and left of the midline of the spinal cord.

All lead contacts and conductors are electrically insulated by a suitable insulating material which is safe for implantation in the human body. The distal contact electrodes may have variable contact surface area as well as variable spacing between electrodes. The number of electrodes may be varied as well.

Electrode polarity refers to activation of lead electrode by assigning positive or negative charge to the electrode. Polarity can include as few as two electrodes per lead (one positive, one negative) on up to as many electrodes as are contained on the lead (with at least one electrode positive and at least one electrode negative). Additional electrodes can be added or substituted to improve coverage area and maximize the treatment.

Lead electrode systems may be percutaneous as described in U.S. Pat. No. 4,044,774 or wider (paddle) systems maybe inserted surgically through a laminotomy or laminectomy incision as described in U.S. Pat. Nos. 3,822,708, and 3,654,933, which are hereby incorporated by reference in their entirety. If multiple leads are implanted, they may be inserted at the same or different levels and used for more complete stimulation coverage.

Examples of totally external power systems include those systems which are used for temporary trial stimulation. Internally implanted systems include totally implanted generators or can include implanted receivers which are internalized but which receive input from an external power source transmitted through antennae. The external systems are radio frequency power sources which may be used for patients with higher energy requirements.

FIG. 1 illustrates the basic elements of a spinal cord stimulation system. Lead 50 comprises distal end 50a and proximal end 50b. Lead extension connector 19 is comprised of a distal end 19a and a proximal end 19b. Lead extension connector 19 is fitted to the proximal end 50b of lead 50 through the distal end 19a of the lead extension connector 19. This connection is made with conducting terminal connections 9, 10, 11 and 12 at the proximal end 50b of lead 50 fitting inside and surrounded by corresponding terminal connections 19c, 19d, 19e, and 19f on the distal extension connector. Distal extension connector terminals 19c, 19d, 19e and 19f contain tightening screws. Each of terminal connections 19c, 19d, 19e and 19f connects to the corresponding conducting terminal connections of the proximal lead 9, 10, 11 and 12 and each in turn corresponds to a distal external conducting electrode 1, 2, 3 and 4 in the distal lead. For example, terminal connection 19c is connected to tube conducting terminal connection 9 which is in turn connected to distal external conducting electrode 1.

The proximal end 19b of the lead extension connector 19 terminates in prong connectors 19g and 19h which fit into the source of energy transmission 20. Prong 19g and 19h fit into receptacle outlets 20a and 20b within the energy source. Prong connectors 19g and 19h are tightened with external screws.

Several possible sources of energy transmission are also illustrated in FIG. 1. The decision for which energy source is optimum for each individual patient is based on the energy needs and coverage area. In use, implanted systems especially those running multiple leads, use larger amounts of energy and subsequently the internal generator battery must be replaced more frequently. External radio frequency energy sources transmitted through antennae to internal implanted receivers have the ability to run multiple lead systems, and can run multiple channels as well, i.e., two separate leads can receive two separate programs. A totally implanted energy source generator with the capability for multiple channels (i.e. different programs for different leads) may also be used.

A totally implantable internalized generator 20 is shown in FIG. 1. An energy system with internalized receiver 21 which has input for the proximal end of the lead extension similar to 19b is also illustrated. In this embodiment, energy is transmitted through an externally placed antenna 22 with impulses transmitted through the skin of the patient to the receiver 21. When the energy source is an external transmitter 23, electrical impulses are transmitted from 23 through the antenna 22 through the skin to the internalized receiver 21 through the lead extension connector 19 to the spinal cord stimulator lead proximal end 50b and finally to the distal end 50a where stimulation is transmitted to the spinal cord. Implanted receiver 21 is inserted into and enclosed by the human body in the same way as the implanted generator 20. In this embodiment, compatible proximal lead extension connector 19b is inserted into receiver 21 which is implanted under the skin. The connection is made by inserting compatible prong connectors 19g and 19h into compatible inlets 21a and 21b, respectively. Antenna 22 is then placed on the skin externally, overlying the implanted receiver 21 and is connected to the external generator 23. The connection is made by inserting compatible antenna prong connectors 22a and 22b into external generator inlets 23a and 23b, respectively. In operation, radio frequency energy is transmitted from external generator 23 through the antenna 22 into the internalized receiver 21. Radio frequency signals are converted to electrical energy and transmitted through compatible lead extension connector 19 into the lead 50 which stimulates the neural structures underneath.

The results of the following animal studies reveal that spinal cord stimulation, delivered at intensities similar to those employed in humans, strongly suppressed abdominal reflex contractions induced by nociceptive levels of colorectal distention in a freely moving chronic rat model. Moreover, spinal cord stimulation also inhibited the exaggerated visceromotor response to innocuous levels of colorectal distention "intestinal allodynia" observed in animals with sensitized colons. Also, spinal cord stimulation blocks the elevated reflex to innocuous colonic distention in a post-inflammatory model of colonic hypersensitivity.

The underlying mechanisms responsible for the inhibitory effects of spinal cord stimulation in these studies are as yet unresolved. However, one theory suggests synaptic modification in spinal and supraspinal pathways. In support of a central mechanism, spinal cord stimulation suppresses pathological hyperexcitability of wide dynamic range (WDR) spinal neurons after peripheral nerve lesions. Furthermore, evidence in a rodent model of peripheral vasodilation suggests that spinal cord stimulation depresses sympathetic nervous activity. Taken together, these neuronal pathways may activate gating mechanisms to suppress visceral hypersensitivity originating from the gastrointestinal tract. The involvement of higher level central circuits, e.g. a dorsal column-brainstem-spinal loop, has also been implicated in the effects of spinal cord stimulation. Such central pathways may contribute to the effects of spinal cord stimulation in irritable bowel syndrome in these animal studies, though the mechanisms remain unresolved.

Recent studies have shown that spinal cord stimulation also acts to increase blood flow via antidromic activation of sensory afferents to release neuromodulatory substances at the target organ. Such a mechanism may also play a role in the inhibitory effect of spinal cord stimulation on the visceromotor responses induced by colonic distention. However, this appears less likely since previous studies have shown that either colonic inflammation, nociceptive colonic distention in a normal colon or stress-induced degranulation of colonic mast cell causes the release of sensory neurotransmitters such as CGRP and substance P. These sensory neurotransmitters are believed to sensitize mechanosensory afferents and to recruit silent nociceptors to cause an enhanced visceromotor behavioral response to a previously innocuous stimulus, such as luminal distension.

Although spinal cord stimulation has inhibitory effects on neuropathic pain, the question of whether spinal cord stimulation may also alleviate pain classified as nociceptive has not been clearly resolved. Therefore, the studies discussed herein were designed to investigate the effect of spinal cord stimulation on the enhanced visceromotor behavioral response induced by high pressures of luminal distention considered to be nociceptive in the rat colon. In the following studies spinal cord stimulation reduced the enhanced visceromotor behavioral response induced by colorectal distention at 60 mm Hg, which indicates that spinal cord stimulation can reduce the reflex muscular response to visceral pain that is classified as nociceptive. Additionally, the studies examined the ability of spinal cord stimulation to suppress the enhanced viscero-somatic reflexes in intestinal allodynia. In rats with hypersensitive colons produced by low concentrations of acetic acid, which do not cause colonic damage, colorectal distention at low levels (30 mm Hg) induced an enhanced visceromotor behavioral response resembling that seen in a rat with a normal colon following nociceptive levels of colorectal distention spinal cord stimulation alleviated also the allodynic responses in rats with sensitized colons. These findings are substantiated by previous experimental studies in which spinal cord stimulation attenuated tactile allodynia in rats and patients.

Although the exact mechanisms by which acetic acid induces colonic hypersensitivity are unknown, it may be that peripheral receptor sensitization leads to changes in central processing characterized by hyperexcitability of dorsal horn neurons in the spinal cord. Furthermore, spinal cord stimulation may possibly inhibit neurons within the intrinsic ganglia of the enteric nervous system that become sensitized in response to acetic acid and demonstrate hyperexcitability in response to luminal distention. In support of this hypothesis, recent observations have shown that spinal cord stimulation applied at the TI-T2 level depresses the activity generated by intrinsic cardiac neurons, which was most evident after provocation of the cardiac neurons with local ischemia.

The animal studies herein also examined the duration of the effect of spinal cord stimulation. The findings indicate that the inhibition of the enhanced visceromotor behavioral response induced by spinal cord stimulation was not stimulus-locked and persisted after the stimulation was terminated, suggesting that stimulation induces processes that require some time for normalization. For comparison, recent studies have shown that spinal cord stimulation in normal rats shortens spinal WDR cell long-term potentiation induced by C-fiber stimulation from normally 6 hours to 0.5 hour. In a rat model of cutaneous allodynia (increased reactivity to tactile innocuous stimuli) spinal cord stimulation at 60% motor threshold for 30 minutes suppressed this over-reactivity for approximately 30-60 minutes post spinal cord stimulation. Furthermore, spinal cord stimulation of the T1-T2 spinal levels for 15 minutes suppresses activity generated by the intrinsic cardiac neurons for a prolonged period after the stimulus was stopped.

The studies herein also show that within 10 minutes of initiating spinal cord stimulation there was a significant inhibition of the enhanced visceromotor behavioral induced by colonic distention. Taken together, the fairly rapid onset of action and prolonged duration of effect despite cessation of spinal cord stimulation suggests that multiple complex changes in neuronal activity and neurotransmitter release occur in response to spinal cord stimulation rather than a simple conduction block. This is supported by previous studies that have demonstrated that afferent second order neurons and interneurons in the dorsal horn of the spinal cord can be activated by spinal cord stimulation. After short activation by spinal cord stimulation, many neurons in the dorsal horn of the spinal cord exhibited a long lasting inhibition.

In many recent experimental studies, spinal cord stimulation is applied with the same parameters as those used clinically for the treatment of neuropathic and cardiac pain. For example, high thoracic spinal cord stimulation at 90% but not 66% of motor threshold results in a depressed activity generated by the intrinsic cardiac neurons in a dog model. Similarly in a rodent model, low thoracic spinal cord stimulation at 60-90% motor threshold induces cutaneous vasodilation in the hind paw in an intensity-dependent manner. The following animal studies demonstrate the effectiveness of spinal cord stimulation at 90% of the motor threshold, but also investigate the effect of lower levels of spinal cord stimulation with magnitudes between 20% and 90% motor threshold. Although spinal cord stimulation inhibited the enhanced visceromotor behavioral response induced by colorectal distention between 30% and 60% motor threshold, a statistically significantly inhibition was not apparent until stimulus amplitudes of 80% threshold were reached. The greatest inhibition of the visceromotor behavioral response induced by colorectal distention was observed at 90% motor threshold.

The effectiveness of spinal cord stimulation to inhibit the visceromotor behavioral response induced by colorectal distention was observed when the stimulating electrode (the cathode) was positioned at the L1 segment of the spinal cord in the present investigation. However, it may be possible to move the electrode to other sites along the spinal cord to achieve similar results. Also, changing the position of the stimulating electrode in rostal and caudal directions from the L1 segment may produce a greater or lesser inhibitory response.

The following animal studies also considered whether a change in the compliance (or tone) of the colonic musculature may have affected the capability of the animal to respond to colorectal distention and thus may have blunted the distention threshold to stimulate the enhanced visceromotor behavioral response. The finding of a pressure-volume relationship measured after spinal cord stimulation, which almost perfectly overlapped that produced prior to spinal cord stimulation, suggests the inhibitory response of spinal cord stimulation on the enhanced visceromotor behavioral response was not the result of a change in colonic compliance but rather an effect of spinal cord stimulation on the viscero-somatic reflex activity. However, the effects of spinal cord stimulation might be different if the visceral region is hyperactive. For example spinal cord stimulation alleviates the hyperexcitable bladder in patients with multiple sclerosis, even though it only moderately alleviates leg spasticity.

In summary, the following animal studies establish that spinal cord stimulation, applied with the same parameters as those used clinically on humans, depresses reflex activity evoked by visceral nociception in the rat. These studies provide strong support that spinal cord stimulation will be an effective treatment for visceral pain of gastrointestinal origin, functional bowel disorders and irritable bowel syndrome.

Animal Study I

This study is consistent with a model developed for quantifying the level of visceral pain in rats by measuring visceromotor behavioral response induced by colorectal distention. This model has been modified to produce visceral hypersensitivity in rats that resembles that seen in patients with irritable bowel syndrome, through colonic infusion of a low concentration of acetic acid, which causes hypersensitivity in the absence of mucosal damage.

This animal study was designed to investigate spinal cord stimulation as a potential therapeutic for visceral pain of gastrointestinal origin. The overall objective of the current study was to examine the effect of spinal cord stimulation on colonic sensitivity as expressed in the visceromotor behavioral response using a conscious rat model. After chronically implanted stimulating electrodes were placed on the dorsal surface of the spinal cord and L1, it was investigated whether spinal cord stimulation, delivered using parameters similar to those used clinically, affected the enhanced visceromotor behavioral response induced by either nociceptive levels of colorectal distention in normal rats or by innocuous distention in rats with sensitized colons.

1. Materials and Methods 1.1 Animals

Experiments were performed on male Sprague-Dawley rats weighing 200-300 g (Charles Rivers, Wilmington, Mass.), housed under controlled conditions (21° C., 0600-1800 h light/dark cycle) with availability to standard rat chow and water ad libitum. Upon arrival, each rat was placed in its own cage for 7 days and acclimated to the animal facility. To reduce the stress associated with experimentation, each rat underwent a second 7-day period of habituation to the experimental environment. During this acclimatization period, between the hours of 10:00 AM and noon, each day rats were brought into the laboratory environment, weighed, and handled for at least 5-10 minutes by the investigator. Prior to the experiment, the animal was fasted 18-24 hours with free access to water. The Animal Studies Subcommittee and Research and Development Committee approved all animal procedures at the Oklahoma City V.A. Medical Center.

1.2 Electrode Implantation and Spinal Cord Stimulation

Rats were anesthetized with a combination of ketamine (80 mg/kg i.p.) and xylazine (10 mg/kg, i.p.). Throughout the procedure body temperature was maintained at 37° C. using a homeothermic heating blanket (Harvard, Ealing, U.K.). The animals were mounted in a stereotaxic frame (Kopf Tujunga, Calif.), and following a small laminectomy and exposure of the dura at the T12/L1 level, a stimulating electrode (oval cathode 3 mm in length) was chronically implanted into the epidural space. The circular anode (5 mm in diameter) was placed subcutaneously with exposure of the contacts made at the level of the neck. This spinal cord stimulation system has proven dependable in many previous animal studies. The stimulation parameters used for spinal cord stimulation were similar to those used clinically in man and consisted of monophasic rectangular pulses (50 Hz; pulse width 0.2 ms) with intensities varying from 10% to 90% of the motor threshold (tonic contraction of the abdominal muscles). The stimulation current was generated by a 5 Grass standard stimulator via a Grass constant current unit (Grass Instruments, Quincy, Mass.).

1.3 Measurement of visceromolor responses induced by colorectal distention

After recovery from the spinal electrode implant procedure (usually 1 week), rats were examined and those that were neurologically intact were anesthetized with either isoflurane (0.7-1.5%) for 5-15 minutes During this time a strain gauge force transducer (RB Products, Stillwater, Minn.) was sutured (seven stitches, 3-0 silk) to the right external oblique muscle at approximately 1 cm from the linea alba in parallel with the muscle fibers. Following wound closure, the lead wires were secured in place by a single stitch to the back and secured with tape at the base of the tail. The signal from the strain gauge was amplified and recorded on a Grass polygraph (Quincy, Mass.). After a 30 minute post-surgical recovery period, a 10 minute recording period was performed to determine the basal number of abdominal muscle contractions. The colorectal balloon was then distended and the change in number of abdominal contractions recorded.

1.4 Distention Procedure

The colorectal region of the rat was distended by rapidly inflating a 5-cm-long flexible latex balloon which was constructed from a non-lubricated latex condom (Trojan, New York, N.Y.). The balloon catheter was inserted into the colon 11 cm past the anal verge and held in place by surgical tape to the base of the tail. The balloon was inflated to a pressure of either 30 or 60 mm Hg and maintained at this level for 10 minutes. Following each distention, the rat was given a 10 minute recovery period. This technique has proven adequate in several earlier studies.

1.5 Sensitization of the Colon

To sensitize colonic afferents and induce a model of colonic hypersensitivity, a model of transient colonic irritation with a mild intraluminal irritant as described by Langlois et al. (1996) and then modified by Plourde et al. (1997) was used. In fasted rats, a low concentration of acetic acid (0.6%, 1.5 ml) was slowly infused into the colon via a catheter (silastic tube I.D. 0.63 mm) running along side the balloon catheter. At the appropriate time this acetic acid was infused into the colon to sensitize colonic afferents. The visceromotor behavioral response induced by colorectal distention measured 1 hour after acetic acid instillation was significantly enhanced compared to untreated controls.

1.6 Assessment of Colonic Compliance

In a separate group of rats with spinal cord stimulation electrodes implanted as previously described, the normal compliance of the colon was determined using a standard volume-pressure relationship. Water was incrementally added into a balloon catheter inserted into the colorectal region and the pressure developed within the balloon was measured using a calibrated pressure transducer attached to the Grass polygraph. After spinal cord stimulation the volume-pressure relationship was re-assessed.

1.7 Experimental Design

The experimental design is illustrated in FIG. 2. Following recovery from the spinal implant surgery (1 week), rats underwent visceromotor behavioral response recordings under baseline conditions with the balloon catheter inserted but not distended. The enhanced visceromotor behavioral response's produced by three consecutive colorectal distentions separated by 10 minute recovery periods were then obtained. The rats then underwent spinal cord stimulation for 30 minutes with a predetermined amplitude after which time the three consecutive colorectal distentions separated by 10 minute recover periods were repeated and the visceromotor behavioral response values recorded.

2. Data and Statistical Analysis.

Chart recordings of visceromotor responses were measured manually and the data expressed as the mean ±standard error of the mean (S.E.M.). Statistical significance was assessed using repeated measures analysis of variance (ANOVA) followed by post hoc analysis using a Student's paired or unpaired t-test where appropriate. $P<0.05$ was considered statistically significant in all tests.

3. Results 3.1 Effect of Spinal Electrode Placement on Visceromotor Behavioral Response Induced by Colorectal Distention in Normal Rats In a control series of experiments (n=8 rats), it was examined whether implantation of a chronically indwelling spinal electrode had any effect on visceromotor behavioral response under either baseline conditions or in response to colorectal distention. Under baseline conditions, i.e. with the colorectal balloon catheter inserted but not distended, there was no significant effect on the number of abdominal contractions in either the experimental group with the spinal electrode or the control group without electrode implantation. Similarly, there was no significant difference between the non-implanted or electrode implanted rats in the visceromotor behavioral response produced by colorectal distention (data not shown).

3.2 Effect of Spinal Cord Stimulation on Enhanced Visceromotor Behavioral Response Induced by Colorectal Distention in Normal Rats In normal rats, colorectal distention at nociceptive levels (60 mm Hg) produced a marked increase in the visceromotor behavioral response, quantified as an increase in the number of abdominal muscle contractions during a 10-minute distention period (FIG. 2). Initially, the effect spinal cord stimulation at 90% motor threshold was examined and it was discovered in 5 rats that if the colon was distended immediately following spinal cord stimulation, there was a marked inhibition of the enhanced visceromotor behavioral response produced by colorectal distention at 60 mm Hg (FIG. 3). To determine whether 90% motor threshold was indeed the optimal stimulation amplitude of spinal cord stimulation, a subgroup of twenty-four rats was used and a series of experiments completed in which it was investigated whether the inhibitory effect of spinal cord stimulation was dependent on the spinal cord stimulation amplitude. As illustrated in FIG. 4, the most effective inhibition of the visceromotor behavioral response induced by nociceptive colorectal balloon distention (60 mm Hg) occurred at between 80 and 90% of motor threshold. At 30-60% of motor threshold, the visceromotor behavioral responses were slightly attenuated by spinal cord stimulation but the responses were not statistically different from those induced by colorectal distention observed prior to spinal cord stimulation. Based upon these findings, all subsequent experiments were performed with spinal cord stimulation at 90% of motor threshold. The animals displayed no signs of pain or other discomfort during spinal cord stimulation at any of the amplitudes used in the present studies.

In the next part of the study, the duration of the inhibitory response induced by spinal cord stimulation at 90% motor threshold was examined. In these experiments, a colorectal distention (60 mm Hg) was performed prior to spinal cord stimulation and the visceromotor behavioral response was measured spinal cord stimulation was then applied for 30 minutes and the colorectal balloon distentions were repeated at 10, 30, 50, 70 and 90 minutes post spinal cord stimulation and the visceromotor behavioral responses determined. In this study, spinal cord stimulation caused a significant inhibition of the enhanced visceromotor behavioral response for 70-90 minutes post spinal cord stimulation (FIG. 5).

3.3 Effect of Spinal Cord Stimulation on Colonic Compliance

Figure 6:
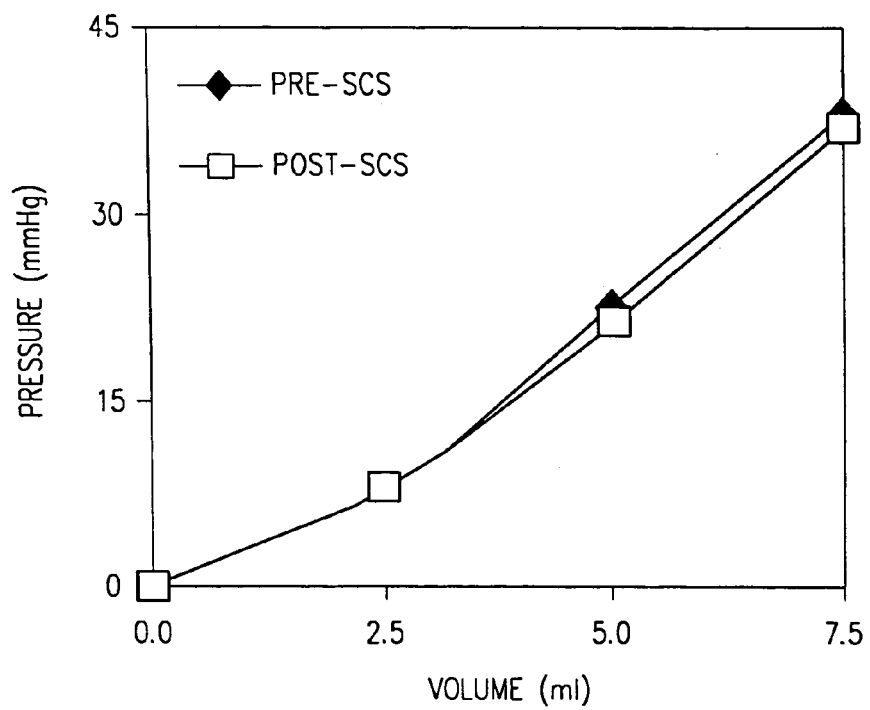
FIG. 6 illustrates the effect of spinal cord stimulation (90% motor threshold) on the compliance of the colonic musculature. The pressure-volume relationship illustrates that following spinal cord stimulation the compliance of the colon was identical to that measured under control non-stimulated conditions.

A change in the compliance (or tone) of the colonic musculature can alter the capability of the animal to respond to colorectal distention, i.e. alter the distention threshold that stimulates the visceromotor behavioral response. Therefore, a series of control experiments were performed in four rats to determine whether the attenuation in the visceromotor behavioral response produced by spinal cord stimulation was the result of a change in colonic compliance. As illustrated in FIG. 6, the pressure-volume relationship measured after spinal cord stimulation was almost perfectly overlapping that produced prior to spinal cord stimulation.

Figure 7:
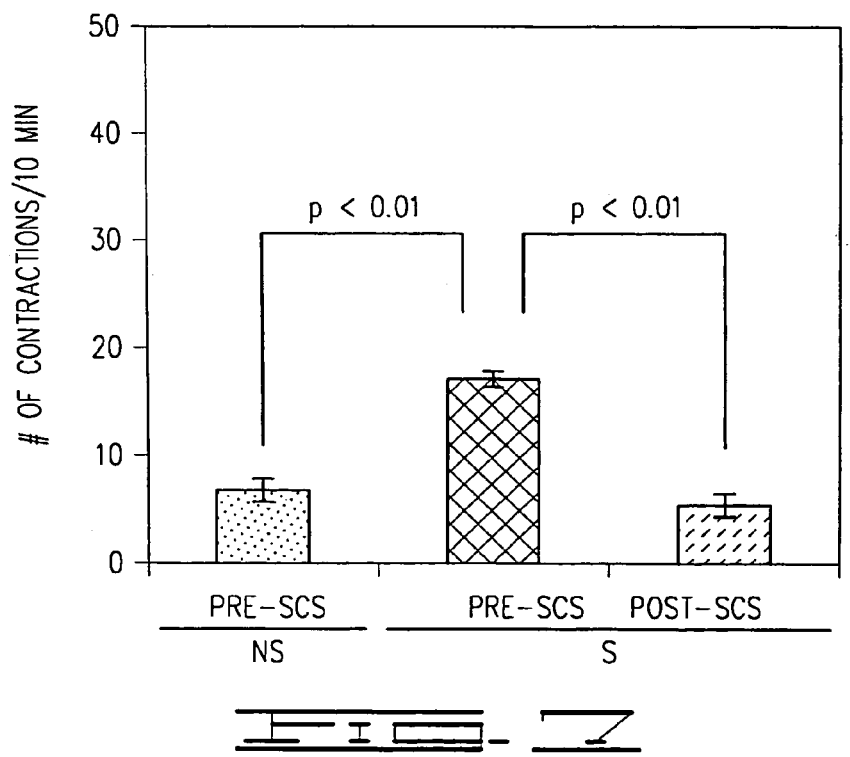
FIG. 7 illustrates the effect of spinal cord stimulation (90% motor threshold for 30 minutes) in rats with sensitized colons. Intracolonic administration of acetic acid (0.6%) caused an increased in the number of abdominal muscle contractions induced by low levels of colonic distention (30 mm Hg for 10 minutes) compared to that seen in rats with non-sensitized colon. The exaggerated visceromotor response was inhibited by spinal cord stimulation.

3.4 Effect of Spinal Cord Stimulation on the Visceromotor Behavioral Response Induced by Colorectal Distention Following Sensitization of the Colon with Acetic Acid The goal of the final series of experiments was to attempt to mimic the clinical situation and determine whether spinal cord stimulation inhibits colonic hypersensitivity. In six rats with spinal cord stimulation implants, innocuous colorectal distention (30 mm Hg) produced a small but significant increase in the visceromotor behavioral response. However, following intracolonic administration of acetic acid (0.6%, 1.5 ml), although there were no significant effect on the baseline number of abdominal contractions, there were a significantly greater number of abdominal muscle contractions in response to low levels of colorectal distention (30 mm Hg). Following spinal cord stimulation in rats with sensitized colons there was a significant decrease in the visceromotor behavioral response to levels that resembled those seen prior to sensitization (FIG. 7).

Animal Study II

1. Introduction

This study is consistent with a model developed for quantifying the level of visceral sensation in rats by measuring visceromotor behavioral response induced by colorectal distention. This model has been modified to produce a post-inflammatory visceral hypersensitivity in rats that resembles that seen in patients with IBS that have recovered from an acute colonic inflammation, through colonic infusion of trinitrobenzenesulfonic acid. Animal study I discussed herein shows that in response to sensitization, innocuous colorectal distention evokes a visceromotor behavioral response, which resembles that induced by nociceptive stimuli in non-sensitized rats. These findings indicate that alterations in neuronal activity within the spinal cord may be involved in processing information from the colon, and that induced abnormalities in spinal neuronal processing may lead to the development of visceral hypersensitivity. Therefore, this study is designed to determine whether spinal cord stimulation has any affect in a rodent model of the post-inflammatory colonic hypersensitivity.

2. Materials and Methods 2.1 Animals

Experiments were performed on male Sprague Dawley rats (Charles Rivers, Wilmington, Mass.), housed under controlled conditions (21° C., 0600-1800 light/dark cycle) with availability to standard rat chow and water ad libitum. Upon arrival, each rat was single-housed for 7 days and acclimated to the animal facility. To reduce the stress associated with experimentation, each rat underwent a second 7-day period of habituation to the experimental environment. During this acclimatization period, between the hours of 10:00 AM and noon, each day rats were brought into the laboratory environment, weighed, and handled for at least 5-10 minutes by the investigator. Prior to the experiment, the animal was fasted 12-18 hours with free access to water. The study was approved by the Oklahoma City Veterans Affairs Medical Center Animal Care Sub-Committee in accordance with the provisions of the U.S. Animal Welfare Act (1966 and amendments), and as described in the Guide for Care and Use of Laboratory Animals, ILAR Commission on Life Sciences (AAALAC-International Guidelines) (ILAR 1996).

2.2 Induction of Colonic Inflammation

After the acclimation period, rats were fasted overnight (12-18 hours). The rats were then brought to the laboratory and briefly anesthetized with isoflurane (5%). While sedated, the rats received an enema (8.0 cm from anus, flexible tubing ID 3.0 mm) of either trinitrobenzenesulfonic acid (TNBS) (50 mg/kg, 0.5 ml, 25% EtOH) or saline. To minimize loss of the liquid enema, the hindquarters of the rates were elevated until consciousness was regained. The rats were then returned to their home cage. Experiments were performed either during active inflammation (day 3) or following recovery from the inflammatory insult (day 30).

2.3. Assessment of Colonic Damage and Inflammation

Morphological Scoring: The morphological score was determined by a qualified blinded observer using 0-5 rating scale developed by Morris et al., (1989). A number was assigned for each tissue sample where 0=no damage, 1=localized hyperemia but no ulcers, 2=ulcers with no significant inflammation, 3=ulcers with inflammation at one site; 4=two or more sites of inflammation and/or ulceration, 5=two or more major sites of inflammation and ulceration, or one major site of inflammation and ulceration extending greater than 1 cm along the colon.

Myeloperoxidase (MPO) Activity: MPO is an enzyme that is released by nuetrophils in tissue under inflammatory conditions. Increased MPO activity shows a direct correlation to the severity of inflammatory damage. MPO activity was measured using spectrophotometric analysis via an ELISA reader. Briefly, in this assay 10 µl samples along with horseradish peroxidase (HRP) standards were placed into duplicate wells of ELISA microtiter plates. The peroxidase substrate (3,3', 5,5' tetramethylbenzidine; TMB) was added to each well to initiate an enzymatic reaction. After 10 minutes, the reaction was stopped by adding 100 µl of 0.1 8M $H_2 5 0u$. An ELISA reader was used to measure the optical density of converted substrate and MPO activity was quantified as ng/100 µl sample. This calculation was then converted to reflect MPO activity as ng/g wet weight tissue.

2.4 Electrode Implantation and Spinal Cord Stimulation

Rats were anesthetized with 1.5-3.0% isoflurane and the surgery site was shaved and sterilized. Throughout the procedure, body temperature was maintained at 37° C. using a homeothermic heating blanket (Harvard, Ealing, U.K.). Following a small laminectomy and exposure of the dura at the T12/L1 level, a stimulating electrode (oval cathode 3 mm in length) was chronically implanted into the epidural space. The circular anode (5 mm in diameter) was placed subcutaneously with exposure of the contacts made at the level of the neck. This spinal cord stimulation system has proven dependable in many previous animal studies. The stimulation parameters used for spinal cord stimulation were similar to those used clinically in man and consisted of monophasic rectangular pulses (50 Hz; pulse width 0.2 ms) with an intensity of 90% of the motor threshold (tonic contraction of the abdominal muscles). The stimulation current was generated by a Grass standard stimulator via a Grass constant current unit (Grass Instruments, Quincy Mass.).

2.4 Measurement of Visceromotor Responses Induced by Colorectal Distention

After recovery from the spinal electrode implant procedure (3-7 days), rats were examined and those that were neurologically intact (bilateral response to touch and pinch, complete motor function) were anesthetized with isoflurane (0.7-1.5%) for 5-15 minutes. During this time a strain gauge force transducer (RB Products, Stillwater, Minn.) was sutured (seven stitches, 3-0 silk) to the right external oblique muscle at approximately 1 cm from the linea alba in parallel with the muscle fibers. Following wound closure, the lead wires were secured in place by a single stitch to the back and secured with tape at the base of the tail. The signal from the strain gauge was amplified and recorded on a Grass Polygraph (Quincy, Mass.). After a 30-minute post-surgical recovery period, a 10-minute recording period was performed to determine the basal number of abdominal muscle contractions. The colorectal balloon was then distended and the change in number of abdominal contractions recorded.

2.5 Distention Procedure

The colorectal region of the rat was distended by rapidly inflating a 5 cm long flexible latex balloon which was constructed from a non-lubricated latex condom (Trojan, New York, N.Y.). The balloon catheter was inserted into the colon 11 cm past the anal verge and held in place by surgical tape to the base of the tail. The balloon was inflated to a pressure of 30 mm Hg and maintained at this level for 10 minutes. Following each distention, the rat was given a 10-minute recovery period. This distention procedure was performed as two series of triplicate distentions. The first series was performed following recovery from the visceromotor behavioral response instrumentation. The second series was performed following spinal cord stimulation. This technique has proven adequate in several earlier studies.

2.6 Data and Statistical Analysis

Chart recordings of visceromotor responses were measured manually and the data expressed as the mean±standard error of the mean (S.E.M.). Statistical significance was assessed using repeated measures analysis of variance (ANOVA) followed by post hoc analysis using a Student's paired or unpaired t test where appropriate. $P<0.05$ was considered statistically significant in all tests.

3. Results

Compared to saline enema treated control rats, within 3 days of the TNBS 50 mg/kg in 50% ethanol) enema, there was an active colonic inflammatory response as demonstrated by an increase in the colonic damage score and elevated levels of myeloperoxidase activity derived from inflammatory cells. However, 30 days after the TNBS enema there was a complete recovery from the colitis. Specifically, on day 30 the colonic damage and myeloperoxidase activity returned to levels that were not statistically different from saline enema treated controls.

3.1 Effect of Colonic Inflammation Induced by TNBS on Colonic Sensitivity to Mechanical Distention In the current study the level of colonic sensitivity in response to luminal distention was determined by measurement of a viscero-somatic behavioral response quantified as the number of abdominal muscle contractions during a 10-minute distention of the colon using a constant pressure of 30 mm Hg. Active colonic inflammation induced by TNBS significantly ($p<0.001$) increased in the number of abdominal muscle contractions induced by low levels of colonic distention compared to that seen in saline enema treated control rats. However, in the absence of colonic inflammation (day 30 post TNBS enema), there was a persistent and significant ($p<0.001$) increase in the number of abdominal muscle contractions induced by colonic distention (30 mm Hg for 10 minutes) compared to that seen in control rats.

3.2 Effect of Spinal Cord Stimulation on the Exaggerated Visceromotor Behavioral Response Induced by Colonic Distention In rats with colonic hypersensitivity induced by active inflammation or following recovery from the inflammatory insult, spinal cord stimulation (90% threshold, 50 Hz, 0.2 ms, 30 minutes) had quite different effects. The results demonstrated that spinal cord stimulation caused a significant inhibition of post-inflammatory colonic hypersensitivity as demonstrated by a reduced number of abdominal muscle contractions induced by low levels of colonic distention. However, spinal cord stimulation had no inhibitory effect on colonic hypersensitivity produced in response to active TNBS-induced colitis.

The present inventive treatment and methods have been discussed primarily in terms of treatments for visceral pain of gastrointestinal origin, functional bowel disorders and irritable bowel syndrome. It is anticipated and expected, however, that these same treatments would be effective for other conditions that cause pelvic pain and discomfort including that originating in or relating to bladder, gastrointestinal and gynecological conditions.

Thus, the present invention is well adapted to carry out the objects and attain the ends and advantages mentioned as well as those inherent therein. While preferred embodiments of the present invention have been illustrated for the purposes of the present disclosure, changes in the arrangement and construction of parts and the performance of steps can be made by those skilled in the art, which changes are encompassed within the scope and spirit of the present invention as defined by the appended claims.

What is claimed is:

1. A method of treating a functional bowel disorder comprising electrically stimulating the spinal cord until a symptom associated with the functional bowel disorder is relieved and wherein said step of stimulating the spinal cord is sufficient to inhibit inflammation and suppress abdominal reflex contractions.

2. The method of claim 1 wherein the functional bowel disorder is irritable bowel syndrome.

3. The method of claim 2 further comprising suppressing pain associated with irritable bowel syndrome.

4. The method of claim 3 wherein the suppression of pain persists after completion of the step of electrically stimulating the spinal cord.

5. The method of claim 1 wherein the stimulating step is performed at a level greater than about 80% of motor threshold.

6. The method of claim 1 wherein said step of stimulating the spinal cord decreases myeloperoxidase activity.

7. The method of claim 1 wherein said step of stimulating the spinal cord produces changes in neuronal activity and neurotransmitter release occur.

8. The method of claim 1 further comprising:
implanting a lead comprised of two electrodes into the epidural space overlying the spinal cord;
connecting the lead to a lead extension connector;
connecting the lead extension connector to a power source capable of generating electrical power; and
energizing the power source for a period of time sufficient to suppress said symptom of gastrointestinal origin.

9. The method of claim 8 further comprising varying at least one characteristics of the electrical power generated by the power source.

10. A method of suppressing pain of gastrointestinal origin comprising:
implanting a lead comprised of two electrodes into the epidural space overlying the spinal cord;
connecting the lead to a lead extension connector;
connecting the lead extension connector to a power source capable of generating electrical power; and
energizing the power source for a period of time sufficient to suppress the pain of gastrointestinal origin and wherein said step of energizing the power source is sufficient to inhibit inflammation, suppress abdominal reflex contractions and decrease myeloperoxidase activity.

11. The method of claim 10 wherein the pain of gastrointestinal origin is associated with a functional bowel disorder.

12. The method of claim 11 wherein the functional bower disorder is irritable bowel syndrome.

13. The method of claim 10 further comprising varying at least one characteristic of the electrical power generated by the power source.

14. The method of claim 13 wherein one characteristic of the electrical power that is varied is amplitude.

15. The method of claim 13 wherein one characteristic of the electrical power that is varied is pulse width.

16. The method of claim 13 wherein one characteristic of the electrical power that is varied is rate.

17. The method of claim 10 wherein said step of energizing the power source provides an electrical signal sufficient to suppress abdominal cramps and further comprising the step of identifying at least one of the following electrical signal characteristics for a specific patient: amplitude, pulse width, rate and duration of electrical power applied.

18. The method of claim 10 wherein the pain suppression persists when the power source is no longer energized.

19. The method of claim 18 wherein the energizing step is performed at a level greater than about 80% of motor threshold.

20. The method of claim 10 wherein changes in neuronal activity and neurotransmitter release occur.

21. A method of treating irritable bowel syndrome comprising:
providing a spinal cord stimulating device; and
stimulating a spinal cord to suppress pain associated with irritable bowel syndrome and to inhibit inflammation, suppress abdominal reflex contractions and decrease myeloperoxidase activity.

22. The method of claim 21 wherein suppression of pain persists after completion of use of the spinal cord stimulating device.

23. The method of claim 21 wherein said step of stimulating a spinal cord is carried out for a period of time sufficient to suppress abdominal cramps associated with irritable bowel syndrome.

24. The method of claim 21 further comprising varying an electrical power component of the spinal cord stimulation device.

25. The method of claim 24 wherein the electrical power component that is varied is amplitude.

26. The method of claim 24 wherein the electrical power component that is varied is pulse width.

27. The method of claim 24 wherein the electrical power component that is varied is rate.

28. The method of claim 21 wherein the stimulating step is performed at a level greater than about 80% of motor threshold.

29. The method of claim 21 wherein changes in neuronal activity and neurotransmitter release occur.

* * * * *